United States Patent [19]

Miyata

[11] Patent Number: 4,667,663
[45] Date of Patent: May 26, 1987

[54] INTRAMEDULLARY NAIL USED TO UNITE SEPARATED FRAGMENTS OF FRACTURED LONG BONE

[76] Inventor: Keizo Miyata, 5-20, Nakajimadori 3-chome, Chuo-ku, Kobe, Japan

[21] Appl. No.: 630,646

[22] Filed: Jul. 13, 1984

[30] Foreign Application Priority Data

Jul. 13, 1983 [JP] Japan .......................... 58-109320[U]

[51] Int. Cl.$^4$ ............................................... A61F 5/04
[52] U.S. Cl. ........................... 128/92 YZ; 128/92 YK; 128/92 YY
[58] Field of Search .............. 128/92 BC, 92 B, 92 R, 128/92 YX, 92 YZ, 92 YV, 92 Y, 92 YW, 92 YY

[56] References Cited

U.S. PATENT DOCUMENTS

| | | | |
|---|---|---|---|
| 2,579,968 | 12/1951 | Rush | 128/92 YZ |
| 2,834,342 | 5/1958 | Yost | 128/92 YX |
| 3,025,853 | 3/1962 | Mason | 128/92 YX |
| 4,055,172 | 10/1977 | Ender et al. | 128/92 BC |
| 4,135,507 | 1/1979 | Harris | 128/92 B |
| 4,169,470 | 10/1979 | Ender et al. | 128/92 BC |
| 4,473,069 | 9/1984 | Kolmert | 128/92 B |
| 4,475,545 | 10/1984 | Ender | 128/92 YY |
| 4,483,335 | 11/1984 | Tournier | 128/92 YY |
| 4,506,662 | 3/1985 | Anapliotis | 128/92 YZ |

FOREIGN PATENT DOCUMENTS 1428653 3/1976 United Kingdom ........... 128/92 BC

Primary Examiner—John J. Wilson
Assistant Examiner—J. Hakomaki
Attorney, Agent, or Firm—Oblon, Fisher, Spivak, McClelland & Maier

[57] ABSTRACT

Disclosed is an intramedullary nail used to unite the separated fragments of a fractured long bone. It has a C-shaped bar-like appearance having a flat front section seen from the direction of insertion as well as a connecting part and, if necessary, a slit in its distal portion. The flat section prevents the rotation of the nail and supports load; the connecting part is used to extract the nail out from the medullary canal; and a stopper for prevention of the rotation is attached to the slit. Such a nail exhibits a stable fixing effect.

5 Claims, 15 Drawing Figures

INTRAMEDULLARY NAIL USED TO UNITE SEPARATED FRAGMENTS OF FRACTURED LONG BONE

BACKGROUND OF THE INVENTION

1. Field of the Invention

This invention relates to a C-shaped nail which is inserted into the medullary canal of a fractured along bone in its longitudinal direction, especially to an intramedullary nail which can accelerate bone union through prevention of displacement and angulation of separated fragments as well as minimization of damage to the bone marrow during its insertion by preventing any rotation of the fragments.

2. Description of the Prior Art

Since the femur is a representative long bone, application of the intramedullary nail of this invention to the femur will be principally described in the following. An increased number of bone fracture accidents in elderly persons have been reported in accordance with an increased proportion of elderly persons. Among these accedents, the most frequent ones are proximal fractures of the femur known as femoral trochanteric fracture, femoral neck fracture and the like. Since a prolonged period of confinement to bed may cause internal complications or secondary diseases, it is ideal that load can be applied to the fractured bone at an early stage before bone union is achieved. For such a purpose, it is necessary that separated fragments are brought into contact with each other on their fractured surfaces to restore the appearance of the original bone before the connected fragments are fixed in their positions over a long period so that natural union of the above contact surfaces can be completed. As the means of fixing the fragment there (A) are nail plate methods represented by the AO angle plate method, the Compression hip screw system and the Massie-type sliding nail-plate method, (B) condylocephalic nailing methods (referred to as C-C method hereinafter) represented by the Ender pin method, the Küntscher nail method and the Harris nail method (described in U.S. Pat. No. 4,135,507), and (C) multiple pinning methods and the like.

The nail plate methods categorized in (A), although exhibiting a relatively good effect in fixing proximal fragments, are insufficiently strong in the fixing of distal fragments and the joint regions between a plate and nails are not free of dynamic weakness. Besides, since it is necessary to develop the fracture site in inserting nails, operation time is prolonged and bone union is delayed due to retarded peripheral blood circulation and breakage of the periosterum. Therefore these methods are disadvantageous to early weight bearing.

The multiple pinning methods categorized in (C) were in use prior to the nail plate methods categorized in (A). These methods are advantageous in that operation is relatively easily performed and operational stress is small. However, in these methods, a very small fixing force is achieved despite insertion of multiple pins and early load bearing is impossible.

From these view points, long nails of the C—C type categorized in (B) have been developed. Such nail has a length almost equal to that of the femur to be treated and is inserted from the distal femoral condyle and passed through the relatively soft medullary canal until its end reaches the proximal femoral head entering the relatively dense cancellous bone located right under the femoral head. Moreover a curved central portion of the nail is brought into contact with the substantia corticalis of the diaphysis. Thus the proximal and the distal fragments are fixed by supporting the inner surface of the substantia corticalis at these points. In the C—C type nail methods, since there is no possibility of directly breaking the substantia corticalis around the fracture site, only a small operational stress is caused. Besides, since a high dynamic intensity in the gravitational direction is realized, load can be applied from a relatively early stage after the operation. However, there is room for improvement since the following problems generally arise: (1) knee disorder due to distal migration, (2) perforation of the femoral head due to proximal migration, (3) varus deformity of the femoral neck due to cutting or the like, (4) external rotation of the distal fragment and (5) fracture of the distal femoral condyle. Degrees and appearances of these problems vary slightly according to the type of nail. For instance, in the Ender pin method in which three thin pins usually are inserted separately while being rotated in the medullary canal, a small space in the medullary canal remains for the latter pin and it can be inserted in an ideal position only with difficulty causing damage to the medullary canal. Besides, since load applied from the proximal side in the longitudinal direction can not be controlled homogeneously, the following troubles may occur: (1) each pin rotates individually causing longitudinal rotation of the distal fragment; (2) part of the pins sink and so protrude from the knee; and (3) part of the pins protrude from the femoral head. Thus clinical problems such as external rotation of the lower limb, varus deformity of the femoral head, knee pain and flexion disturbance of the knee are caused. In contrast, Küntscher nails and Harris nails are relatively thick and rigid nails having the following characteristics. The Kuntscher nail is inserted through a single surface almost without being turned in the medullary canal thereby causing almost no damage to the medullary canal. However, due to its almost circular cross-section, it has a weak spring force as well as a weak rotation resistance and is thereby relatively unsuitable for the fixation of the proximal fragments. The Harris nail, although considered to exhibit a higher rotation-fixing force than the former two, originally has a shape corresponding to the medullary canal and can be inserted only with difficulty due to its rigidity. In addition, there is a high risk of damage to the medullary canal and it therefore is relatively unsuitable for the fixation of the proximal fragments. The backgrounds of these characteristics will be further described below. The femur has a physiologic anterior curvature, while the main curves of long nails of the C—C type present C-curves as viewed from the lateral surface (L-surface). In other words, the curve of the Küntscher nail corresponds to the above C-curve. However, it is said to be ideal that the Küntscher nail be inserted in a straight direction seen from the L-surface of the femur the C-curve of the Küntscher nail not corresponding to the C-curve of the femur. In such a nail with a secured straightness, its end easily reaches the femoral head thereby exhibiting a good fixing performance. However, since the C-curve of the nail corresponds to the anterior curvature of the femur as mentioned above, the nail tends to obtain a stable attitude by rotating in the medullary canal and the distal fragment rotates due to the rotation of the nail. This is termed external rotation as mentioned before. If such external rotation occurs, a defective reposition is achieved and early load bearing will cause various harmful effects. Here concerning the distal fragments, both the Kuntscher nail and the Harris nail can not be considered to exhibit a sufficient rotation-preventing effect due to the following reasons: (1) the mechanical intensity of the cancellous bone right under the femoral head is weak in a direction perpendicular to the bone trabecula; and (2) the sectional shapes and the sizes of the ends of these nails are an extention of their central portions and these ends have no special rotation-preventing functions. The Harris nail has not only a C-curve corresponding to the above mentioned physiologic anterior curvature but also a distortion corresponding to a physiologic frontward distortion located above the trochanter. That is to say, it has an appearance almost similar to the shape of the medullary canal of the femur. Such an appearance, although seeming to be reasonable when considered only from the situation achieved after the nail is inserted in the medullary canal, is not so when considering the difficulty in inserting such a curved nail into the medullary canal, having anterior curvature and anteversion in the longitudinal direction. Such a three-dimensional nail as the Harris nail having a C-shaped curve and an end distortion perpendicular to the surface of the C-curve, can not be inserted straight without damaging a wide area of the bone marrow. Besides, it can not be twisted and inserted in accordance with the above distortion without disturbing the medullary canal to a substantial degree. Therefore, there is a possibility not only that a physiologically unfavorable effect is caused due to damage to the bone marrow but also that only an insufficient fixing or rotation-preventing effect can be achieved.

In conclusion, the conventional C—C type nail has a purpose only of making its shape similar to the physiologic shape of the femur, and is not sufficiently designed to satisfy both facilitated insertion and a good rotation-preventing effect.

SUMMARY OF THE INVENTION

It is an object of the present invention to provide a novel nail of the C—C type that can exhibit a more than satisfactory effect of suppressing the rotation of the distal fragment. Another object of this invention is to provide a C—C type nail which can enhance such a rotation-preventing effect without lessening the efficiency of the insertion. The other purposes will become apparent from the following description.

The C—C type nail according to this invention has a C-curved bar-like appearance as a whole. A flat section expanded in the direction perpendicular to the surface including the above curved line is provided at the front end in the direction of insertion and a connecting part for extracting the nail is provided in the back end in the direction of insertion.

DETAILED DESCRIPTION OF THE INVENTION

Figure 1:
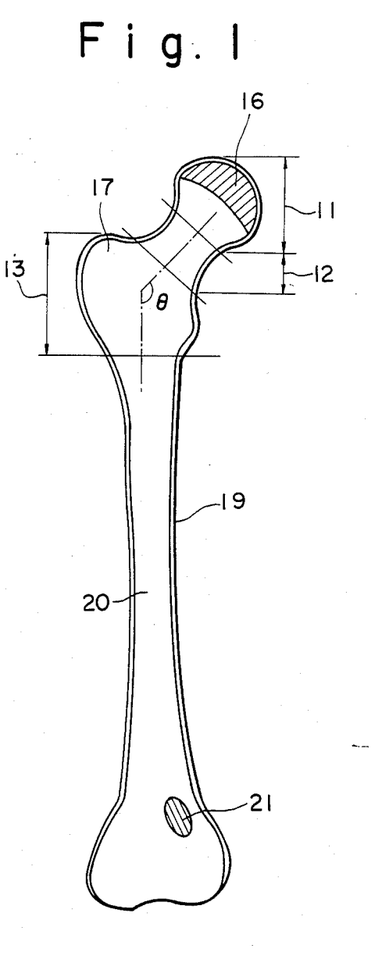
FIG. 1 is a front view illustrating the anterior or posterior (A-P) surface of the femur.
Figure 2:
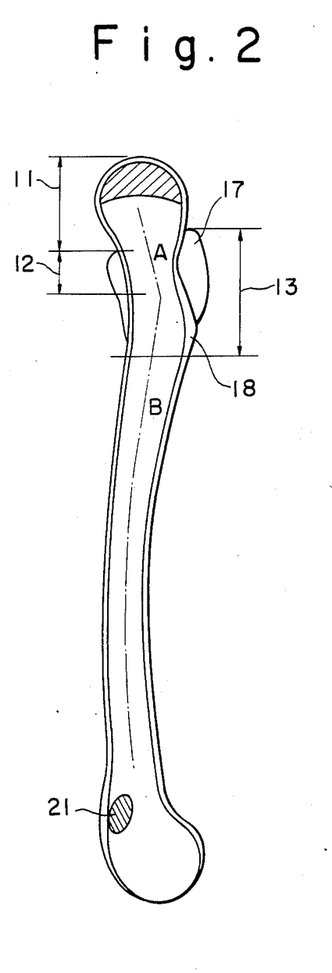
FIG. 2 is a lateral view illustrating the lateral (L) of the femur.
Figure 11:
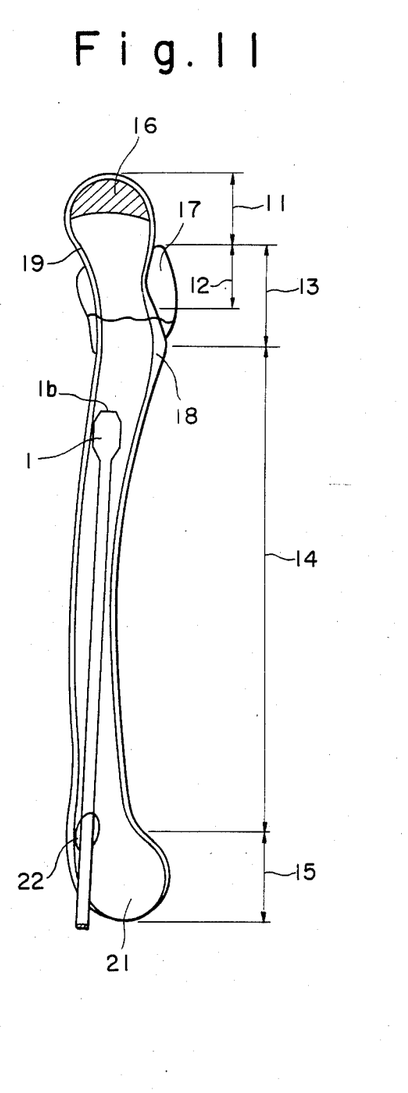

The structure of the femur is an indicated in FIGS. 1 and 2. The femur is divided into a femoral head indicated by the symbol 11, a femoral neck indicated by the symbol 12, a femoral trochanter indicated by the symbol 13, a diaphysis indicated by the symbol 14 (FIG. 11) and a femoral condyle indicated by the symbol 15. The symbol 16 indicates a dense cancellous bone; the symbol 17, a trochanter major; the symbol 18, a trochanter minor; the symbol 19, a substantia corticalis; and the symbol 20, a spongiose. The femur has a neck angle ($\theta$) on the A-P surface as indicated by a chain line in FIG. 1, as well as anteversion and aterior curvature as indicated by a chain line in FIG. 2. As for the bone construction of the femur, it consists of the peripheral hard cortex (19) and the inner soft spongiose (20). Here, the spongiose located below the femoral head is relatively soft and that located immediately below the femoral head is very hard.

The C—C nail (condylo-cephalic nail) is usually inserted from a medial condyle (21) located in the lower portion of the femul until its end reaches the hard spongiose located immediately below the femoral head thereby mainly fixing fractures located toward the center from the diaphysis.

In performing intramedullary fixation of femoral fractures located toward the center (trochanteric or intracapsular fracture) by inserting a nail into the medullary canal, contact area between the spongiose and the nail is much smaller in a proximal fragment than in a distal fragment. This difference in contact area leads to difference in fixing force causing unbalance in fixing ability. Thus, it has been shown that, since a C—C type nail has a weaker fixing force in the proximal fragment than in the distal fragment owing to its shape, rotational force developed in the distal fragment causes non-fixation between the nail and the proximal fragment thereby causing their rotation. In order to suppress such rotation of the proximal fragment it is necessary to increase the contact area between the nail and the spongiose in the proximal fragment. However, a greater increase in the contact area does not necessarily enhance rotation-preventing effect. For instance, in the nail having a circular cross-section and a maximized surface area, rotation-preventing force will be lost on the curved surface and almost no rotation-preventing effect can be expected. From such view points, the proximal end of the nail should be flat and wider than its central section. Since any rotation of the flat section of a nail of such structure is prevented by the spongiose, the nail itself is free from rotation preventing any rotation between the two fragments accompanying the breakage of the spongiose within the femoral head as well as any deformity of the femoral head.

In providing the end of the nail with a flat section, attention is directed to the direction in which the flat surface should face. Since the nail is provided with such a C-curve as mentioned previously, a applied from above will not bear in a direction completely coinciding with the axis of the nail but will bear from the back surface side of the apex of lordosis toward its inner side, or in such a direction as to decrease the curvature radius of the anterior curvature. Therefore, the nail is required to have a rigidity sufficient to resist the external force. In short, since the load is supported by the end surface of the nail the extreme end of which is buried in the subcapital cancellous bone, the shape of the end should be appropriate for supporting the load. If the shape of the end is inappropriate, there is danger of the end breaking through the substantia corticalis of the femoral head and protruding toward the pelvis. Considering such a load-supporting effect, it is most effective that the above flat surface provided for the preventing of rotation also serves as a load-supporting surface. Accordingly, the flat surface is provided perpendicular to the surface including the curved line. In addition, since the surface of the extreme end of the nail also plays an important role in supporting the load, it goes without saying that it is desirable that the extreme end of the nail has a flat surface rather than being pointed.

The back end of the insertion is provided with a connecting part to which a nail extractor is attached after at the time of operation and completion of bone union. The shape of the connecting part is optional according to the construction and shape of the extractor.

In the following, a description will be given in accordance with the figures.

Figures 3, 4:
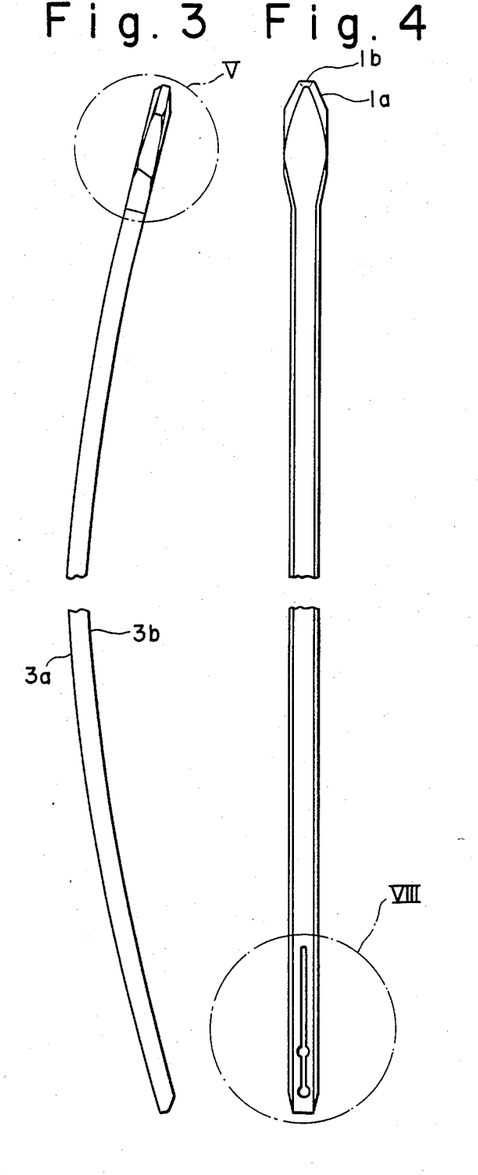
FIG. 3 is a front view of the nail according to this invention corresponding to the A—P surface of the femur.
FIG. 4 is a lateral view seen from the left side of FIG. 3 and corresponding to the L surface of the femur.
Figure 5:
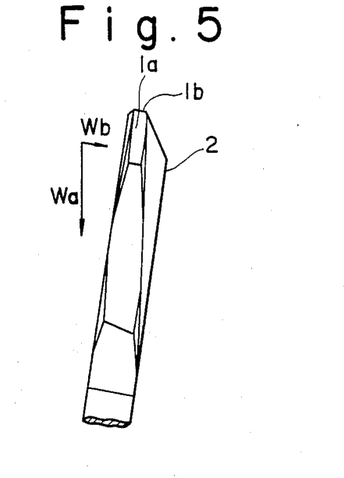
FIG. 5 is a magnified front view of an area surrounded by a circular chain line (V) in FIG. 3.
Figure 6:
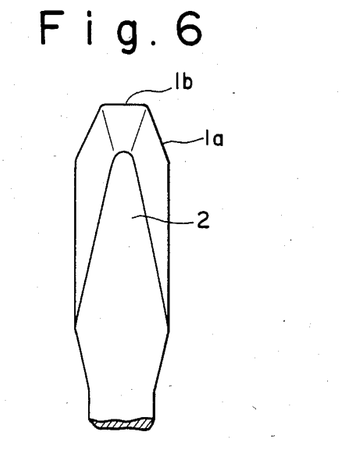
FIG. 6 is a magnified lateral view seen from the right side of FIG. 5.

The nail according to this invention, as shown in FIGS. 3 and 4, has a shaft with a C-shaped curve viewed from the front and an almost linear shape viewed laterally. As shown in FIG. 4, a wide flat section (1) is provided on the side surface of the end of the nail. Although the extreme end of the flat section (1) is tapered in order to facilitate its insertion, it is desirable that the nail has a flat end surface (1b) which can receive a load applied from above as mentioned before. Since an over-sharpened end has the possibility of breaking through the femoral head under load and may decrease the load-supporting function, the end may be of a gently rounded stream line shape. As shown in FIGS. 5 and 6, the radially inner surface of the end of the flat section (1) is provided with a bulge (2), so that the bone marrow receives only a small insertion resistance and so that the bulge (2) on contacting the inner surface of the substantia corticalis or other hard regions can alter its direction in reaction to the contact, thereby exhibiting a self guiding performance. In addition, the outer surface of the end of the flat section (1) can be advantageously be provided with a slightly bulged shape for reduction of insertion resistance.

Owing to the flat surface of the flat section (1) provided in the above described direction, when load (Wa) is applied to the flat section (1) vertically from above as indicated in FIG. 5, a component of force (Wb) corresponding to the inclination angle of a flat surface (1a) works as a bending force on the nail. It has been shown that, owing to the flat surface (1a) provided perpendicular to the surface including the curved line of the nail, the nail has a high load-supporting performance and can sufficiently assist early load bearing after operation. As described above the flat end surface indicated by the symbol (1b) exhibits a load-supporting effect. In the process of bone union, dead tissue at the fracture line is compressed due to the vertial load, causing a tendency to a slight decrease in the length of the femur. As a result, the upper end of the nail tends to protrude toward the pelvis breaking through the femoral-head-side substantia corticalis, and the lower end of the nail tends to protrude toward the knee through the distal insertion opening. Among these protrusions, protrusions toward the pelvis should be avoided necessarily although protrusions toward the knee may be somewhat permissible. The nail of the invention, owing to its expanded end as indicated in the figure, can only with difficulty break through the femoral-head-side substantia corticalis. Besides, the direction of the flat surface (1a) enables the nail to receive a load as an impact force pushing down its end. Therefore, the nail of this invention has no possibility of protruding toward the pelvis, and shows a little protrusion toward the knee at most without causing any pain to the patient.

Figure 7:
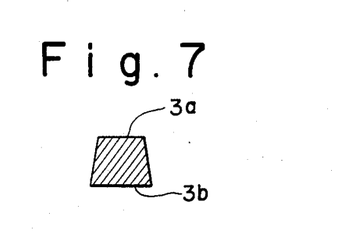
FIG. 7 illustrates the cross section of the intermediate portion of the nail.

Next, as to the intermediate portion (3) of the nail, no special restrictions are provided except that this portion is thinner than the end portion and has a C-shaped curve. However, in order to prevent any rotation of the distal fragment by achieving increased fixing of the fragment, it is desirable that the cross-section of the nail is a flattened circle or a polygon. FIG. 7 illustrates one such shape. As far as all sides and angles of the polygon present straight lines and acute angles, the nail can not be easily rotated because of the contact with the bone marrow. With the above trapezoid having an upper side corresponding to the outer side (3a) of the curve and a lower side corresponding to the inner side (3b), the nail becomes flexible against the curve, and the degree of the curve is slightly decreased during the time when the end of the nail passes through the relatively straight distal fragment facilitating easy insertion. From the time when the end is substantially inserted, the curved state is gradually restored to a C—curve corresponding to the shape of the bone marrow thereby achieving a stable position of insertion.

Figure 8:
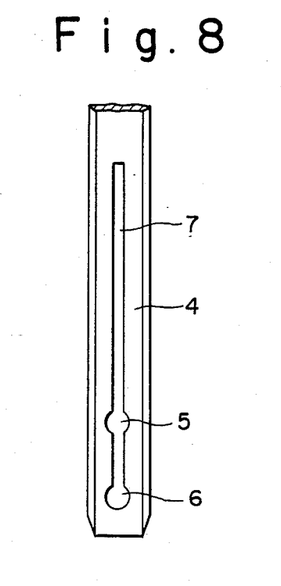
FIG. 8 is a magnified lateral view of an area surrounded by a circular chain line (VII) in FIG. 4.
Figure 9:
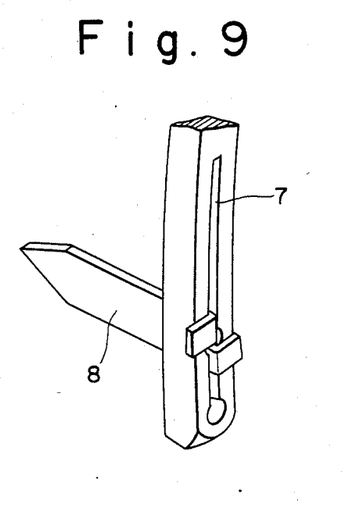
FIG. 9 is an oblique view illustrating the attached condition of a stopper.
Figure 10:
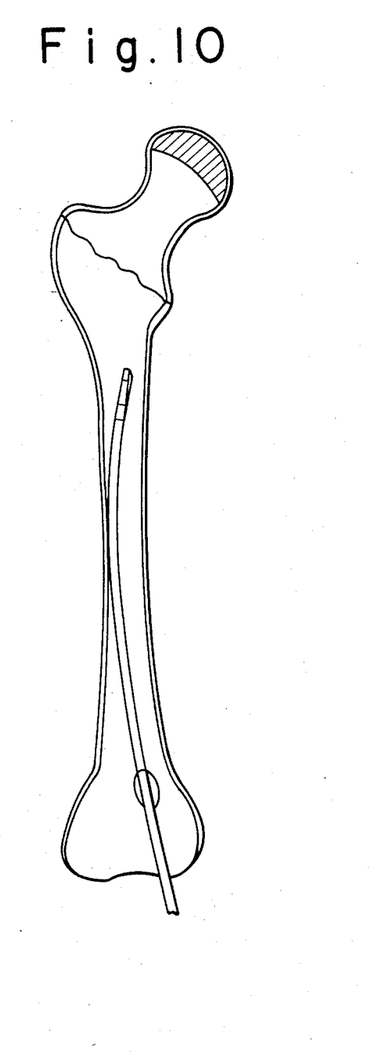
FIGS. 10 through 15 illustrate the steps of insertion of the nail with FIGS. 10, 12 and 14 being front views illustrating the A—P surface of the femur and FIGS. 11, 13 and 15 being lateral views illustrating the L surface of the femur.

Next, description of the lower end portion (4) of the nail will be given. The lower end portion (4) has a slit and an extraction hole to which a nail extractor is to be attached. The shape of the hooking part should be determined according to the construction and shape of a nail extractor. In other words, a nail extractor should be considered according to the shape of the connecting part. Therefore the shape of the connecting part is not absolutely restricted. FIG. 8 illustrates one example of the connecting part. In this example, owing to penetrating holes 5 and 6, a hook-shaped extractor can be inserted easily. A slit (7) is provided so that a stopper (8) is inserted in it. FIG. 9 is an oblique view illustrating the inserted state of the stopper (8). Although insertion of a stopper (8) is not essential, use of a plate-like stopper (8) as illustrated in the figure will increase the rotation resistance of the distal fragment. Accordingly, it is recommended in some cases that a stopper (8) be inserted according to the condition of fracture and the schedule of treatment. Here, the slit (7) is made relatively long in the longitudinal direction of the nail so that the stopper (8) can be maintained in the original position of attachment even if the nail sinks toward the knee as mentioned before. As a result, any impact force is absorbed while preventing the rotation of the distal fragment, and any possibility of a distal fracture which might be caused with a fixing-type stopper is prevented. Besides, the nail can be prevented from penetrating the femoral head. The nail according to this invention, being mainly used for femoral proximal fractures in elderly persons, is not extracted in many cases.

The nail according to this invention, in terms of safety to a human body, corrosion resistance, rigidity, elasticity and the like, is preferably manufactured by the use of a titanium-system alloy such as Ti-6Al-4V However, the material can be selected optionally according to condition and a stainless steel, plastic, ceramics or the like can be used instead. It is a matter of course that a complex-layered construction can be adopted by using a complex material or using different materials for an inner portion and an outer portion.

FIGS. 10 through 15 illustrate different positions of the nail achieved successively when it is inserted into the medullary canal. A wave line crossing the trochanter (13) represents an example of a fracture site.

Figure 12:
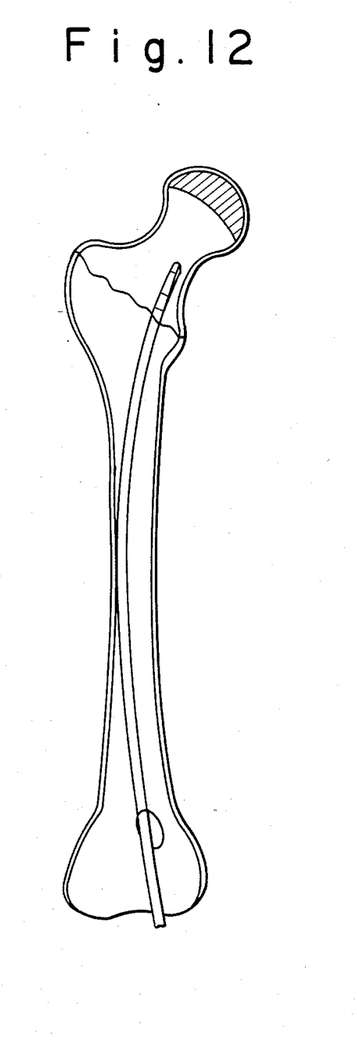
Figure 13:
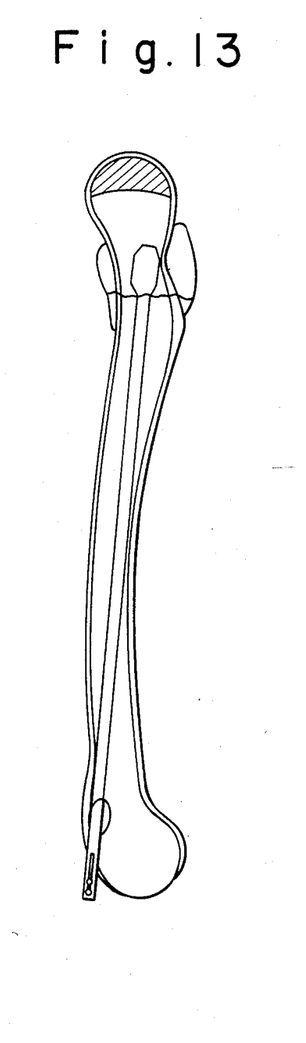
Figure 14:
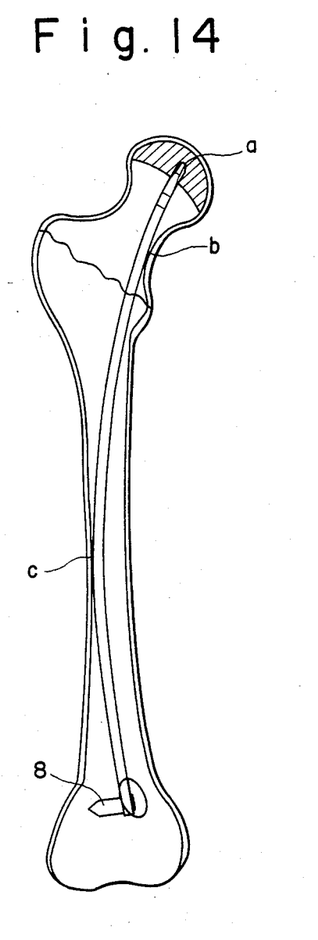
Figure 15:
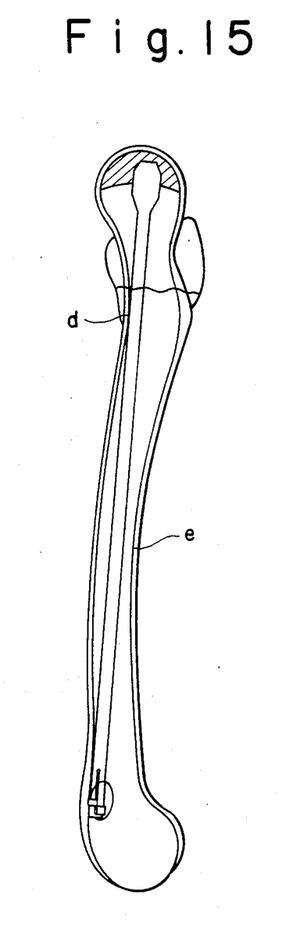

The condyle (15) is provided with an opening (21) for the insertion of the nail by opening a part of the substantia corticalis (19). The nail is inserted, with the end flat section (1) directed upward, in such a manner that the side surface of the femur coincides with that of the nail before being lifted in such a manner that it penetrates the spongiose (20). From the point when the flat surface or left upper shoulder (1a) of the flat section (1) contacts the inner surface of the substantia corticalis (19) (FIG. 10), the nail shifts toward the right seen in FIG. 10 while passing through the spongiose (20). Then from the point when the right upper shoulder (1a) of the flat section (1) contacts the inner surface of the substantia corticalis (19) as shown in FIG. 12, the nail is lifted while shifting toward the left as seen in FIG. 12 until a part of the extreme end of the flat section (1) invades the cancellous bone (16) stopping the movement of the nail. Although the nail is fixed at its invading point (a) located in the cancellous bone (16) as well as contacts (b), (c), (d) and (e) located on the inner surface of the substantia corticalis (19), it does not contact the substantia corticalis (19) at the point (b) in some cases. In other words, it is desirable that the nail has a curvature presenting an orbit connecting these points (a through e) However, the curvature need not necessarily be constant over the whole length of the nail. It should be selected so that insertion of the nail is smoothly performed considering the positional relationships among the points (a), (b), (c) and the opening (21) as well as the aforementioned extention and restoration of the curve of the nail due to its elasticity. Therefore it is recommended in some cases that the curvature be altered around the point (c). An excessively large curvature will cause the nail to bump against the inner surface of the substantia corticalis before the flat section (1) reaches the point (c) located in the narrowest region in the medullary canal, thereby making any further movement of the nail difficult. In order to achieve an excellent state of fixation, it is desirable that the nail be passed near the points (b) and (c) as close as possible to the points (b) and (c). In addition, it is recommended that the nail be passed in a straight state between the opening (21) and the point (c) and that the nail be restored to its curved state in such a manner that it proceeds close to the point (b) due to its elasticity after passing the point (c).

The nail according to this invention, owing to the above construction, causes no adverse influence during its insertion. Besides, it exhibits an excellent fixing performance after being inserted in the medullary canal without causing any troubles such as being rotated or penetrating the femoral head.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A C-shaped bar-like intramedullary nail for a fractured femur, comprising:
    an elongated shaft having a longitudinal curve wherein said curve is a two dimensional curve, whereby said shaft is straight when seen along a radial line of said curve;
    a front insertion end of said shaft, said front end having a flat section defining a direction transverse to both a longitudinal direction of said shaft and a radial line of said curve, said flat section having a width in said transverse direction which is greater than a width of said shaft in said transverse direction, wherein said flat section is tapered in said transverse direction, said taper narrowing toward said front end, and wherein said front end forms a flat end surface;
    a back insertion end of said shaft, said back end including means for extracting said nail from a bone; and
    a radially extending bulge on a radially inner surface of said flat section.

2. The nail of claim 1, wherein said shaft is a polygon in transverse section.

3. The nail of claim 2, wherein said polygon is a trapezoid having a longer side at said inner surface.

4. The nail of claim 1, wherein said means for extracting comprises a longitudinal slot.

5. The nail of claim 4 including a stopper to be inserted in said slot, wherein said slot is longer than the width of said stopper.

* * * * *